US008697126B2

(12) United States Patent
Chen et al.

(10) Patent No.: US 8,697,126 B2
(45) Date of Patent: Apr. 15, 2014

(54) COMPOSITIONS FOR ENTERNAL APPLICATION OF MICROORGANISMS

(75) Inventors: Chyi-Cheng Chen, Binningen (CH); Bruno H. Leuenberger, Rheinfelden (CH); Loni Schweikert, Zuzgen (CH); Ernst Zedi, Reinach (CH)

(73) Assignee: DSM IP Assets B.V., Heerlen (NL)

( * ) Notice: Subject to any disclaimer, the term of this patent is extended or adjusted under 35 U.S.C. 154(b) by 600 days.

(21) Appl. No.: 11/920,555

(22) PCT Filed: May 18, 2006

(86) PCT No.: PCT/EP2006/062416
§ 371 (c)(1),
(2), (4) Date: Feb. 6, 2008

(87) PCT Pub. No.: WO2006/122965
PCT Pub. Date: Nov. 23, 2006

(65) Prior Publication Data
US 2009/0214647 A1  Aug. 27, 2009

(30) Foreign Application Priority Data
May 18, 2005 (EP) .................................... 05010735

(51) Int. Cl.
*A23C 9/12* (2006.01)
(52) U.S. Cl.
USPC .......... 424/475; 424/490; 424/498; 424/93.4; 424/93.45; 426/61; 427/2.14
(58) Field of Classification Search
None
See application file for complete search history.

(56) References Cited

U.S. PATENT DOCUMENTS 5,478,570 A    12/1995  Sunohara et al.
6,326,028 B1 * 12/2001  Nivaggioli et al. ........... 424/481
2004/0120931 A1 * 6/2004  Myatt .......................... 424/93.4
2005/0153018 A1 * 7/2005  Ubbink et al. ................. 426/61
2009/0162322 A1 * 6/2009  Rudolph et al. ............. 424/93.4

FOREIGN PATENT DOCUMENTS

| EP | 1 344 458 | * | 9/2003 | ............ A23K 1/00 |
| EP | 1 344 458 A1 | * | 9/2003 | ............ A23K 1/00 |
| GB | 930 107 | | 7/1963 | |
| JP | 04-041434 | * | 2/1992 | ............ A61K 35/74 |
| JP | H4-41434 | | 2/1992 | |
| JP | 5-186337 | | 7/1993 | |
| JP | H9-241173 | | 9/1997 | |
| JP | 2001-245660 | | 9/2001 | |
| WO | 97/16198 | | 5/1997 | |
| WO | WO 97/16198 | | 5/1997 | |
| WO | WO 97/46224 | | 12/1997 | |
| WO | WO 99/17788 | * | 4/1999 | ............ A51K 35/00 |
| WO | WO 01/12164 | | 2/2001 | |
| WO | WO 2004/022727 | | 3/2004 | |
| WO | WO 2005/117921 | | 12/2005 | |

OTHER PUBLICATIONS

International Search Report for PCT/EP2006/062416 mailed Jul. 17, 2006, three pages.
Notice of Opposition, Apr. 6, 2012, (English translation), pp. 1-11.
Stadler et al, "Optimization of a Formulation Containing Viable Lactic Acid Bacteria," International Journal of Pharmaceutics, vol. 256, 2003, pp. 117-122.

* cited by examiner

*Primary Examiner* — Suzanne Ziska
(74) *Attorney, Agent, or Firm* — Nixon & Vanderhye P.C.

(57) ABSTRACT

The present invention describes a process for the manufacture of a solid composition comprising a microorganism, which process comprises a first step of blending and/or compacting the microorganism with a salt of a medium or long-chain fatty acid to prepare a powderous mixture or compacted granulate, and a second step of providing said powderous mixture or compacted granulate with a coating. The microorganisms are preferably probiotics. The invention also relates to the solid composition obtained by said process and to its use in food.

34 Claims, No Drawings

COMPOSITIONS FOR ENTERNAL APPLICATION OF MICROORGANISMS

This is the U.S. national phase of Int'l Application No. PCT/EP2006/062416 filed 18 May 2006 which designated the U.S. and claims priority to EP 05010735.8 filed 18 May 2005; the entire contents of each of which are hereby incorporated by reference.

DETAILED DESCRIPTION OF THE INVENTION

The present invention relates to compositions, which can be used to supply microorganisms to the intestinal tract. Several problems may be encountered when manufacturing compositions for nutritional or pharmaceutical purposes comprising living microorganisms. Some of these problems are addressed in WO 97/16198. In particular, microorganisms, which are intended to exert their activity in the intestinal tract must be protected against the impact of acid as present in gastric juice. Further, embedded microorganisms in a carrier or protective matrix, which are commonly freeze-dried, tends to be hygroscopic and easy to become caking at ambient storage conditions. This caking effect may impede the processing to solid dosage formulations such as tablets, e.g., by insufficient flowability, and may, further, have negative impact on the storage stability in terms of viability of the microorganisms due to rapid moisture absorption. Flowability of a powderous product may also be influenced by particle size in that a too small particle size may impede flowability and thus, for instance, lead to problem in content uniformity of the active in tablets. Therefore, low hygroscopicity and good flowability are essential features for processing powderous products, e.g. to prepare tablets and capsules, especially powderous products involving microorganisms.

WO 97/16198 discloses compositions of probiotic microorganisms such as *Lactobacillus* species in a gastric juice resistant matrix. The compositions are prepared by mixing dried microorganisms with a gastric juice resistant matrix component, compacting the mixture and dry-granulating the mixture obtained. Optionally, the so-obtained granulate is submitted to a further dry-granulation step to provide a gastric juice resistant coating on the granulate.

It has been found that the known formulation procedures, such as the use of granulate prepared by the process of WO 97/16198 do not always lead to tablets showing satisfying properties, e.g. tablet hardness and tablet bending strength so that the tablets cannot be readily damaged during handling.

In accordance with the present invention it has been found that microorganisms can be processed to granulates or powders having superior properties for tabletting purposes, particularly lack of hygroscopicity and good flowability, and from which tablets having satisfying handling properties can be prepared by a novel process which comprises a first step of blending and/or compacting the microorganism with a salt of a medium or long-chain fatty acid to prepare a powderous mixture or compacted granulate, and a second step of providing said powderous mixture or compacted granulate with a coating.

Thus, in one aspect, the invention relates to a process for the manufacture of a solid composition comprising a microorganism, wherein in a first step a mixture of a microorganism and a salt of a medium or long-chain fatty acid is compacted and granulated; whereupon in a second step a coating is provided on said granulate.

In another aspect, the invention is concerned with a process for the manufacture of a solid composition comprising a microorganism, in which process in a first step a microorganism is blended with a salt of a medium or long-chain fatty acid to produce a powderous mixture, whereupon in a second step, the particles of the powderous mixture are provided with a coating; and with compositions obtainable by said process.

In still another aspect, the present invention is concerned with solid compositions containing a microorganism which is coated by or embedded within a salt of a medium or long-chain fatty acid, wherein the microorganism has, optionally, a first coating layer below the coating by the salt of the medium or long-chain fatty acid; and which composition has an outer coating which contains substantially no material which is present inside the composition.

The coating can be continuous or discontinuous depending on the amount of coating material and coating conditions. Without wanting of being bound by the theory it is assumed that some particles may be coated partially or completely and then agglomerated to form a larger particle. The agglomerated particles are then coated. Thus, the coating process would inherently involve a granulation process. In fact, such granulation process would be desirable in that it makes particles larger and improves the powder flow.

The process of the present invention may be carried out with any microorganism or mixtures thereof. The term microorganism as used herein denotes any solid form of microorganism including freeze-dried preparations, which typically comprise auxiliary agents such as carbohydrates and/or proteins, and preparations wherein the microorganism is coated by or embedded in a matrix material, e.g., proteins, maltodextrins, trehalose and/or ascorbic acid. In the context of the invention, "a microorganism" means at least one microorganism. Preferably, the microorganisms are those that can be supplied to the intestinal tract as a nutritional supplement or pharmaceutical agent or food additive. More preferably, the microorganism is a probiotic or mixtures thereof. A probiotic is defined herein as a live microbial strain, which beneficially affects the human host cell by improving its microbial balance. Preferred probiotics are isolated strains of *Bifidobacterium, Lactobacillus, Propionibacterium, Enterococcus*, and mixture thereof. More preferred probiotic species are *Bifidobacterium infantis, Bifidobacterium longum, Bifidobacterium animalis, Bifidobacterium lactis, Lactobacillus acidophilus, Lactobacillus rhamnosus, Lactobacillus casei, Lactobacillus paracasei, Lactobacillus helveticus*, and mixture thereof. According to a preferred embodiment, the microorganism comprises as active ingredient at least one of the following probiotics: *Lactobacillus acidophilus* strain LAFTI® L10 deposited at the CBS under accession number CBS 116411, *Lactobacillus casei* strain LAFTI® L26 deposited at the CBS under accession number CBS 116412 and LAFTI® B94, which is a *Bifidobacterium animalis*. According to a preferred embodiment, the probiotic consists of a biologically pure culture or substantially biologically pure culture of at least said deposited strain(s). According to a more preferred embodiment, the probiotic consists of a biologically pure culture or substantially biologically pure culture of at least said deposited strain(s) in combination with any other valuable probiotic. According to an even more preferred embodiment, the probiotic is selected from the group consisting of *Bifidobacterium infantis, Bifidobacterium longum, Bifidobacterium lactis, Bifidobacterium animalis, Lactobacillus acidophilus*, preferably *Lactobacillus acidophilus* LAFTI® L10 CBS 116411, *Lactobacillus rhamnosus, Lactobacillus casei*, preferably *Lactobacillus casei* LAFTI® L26 CBS 116412, *Lactobacillus paracasei* and *Lactobacillus helveticus*. Even more preferably, the microorganism is *Lactobacillus acidophilus* CBS 116411 and/or *Lactobacillus casei* CBS 116412 and/or a *Bifidobacterium animalis*.

In the first step of the process of the present invention, the microorganism is mixed, or mixed and compacted with a non-toxic salt of a medium or long-chain (e.g., $C_{10-30}$—) fatty acid such as a stearate or palmitate. Particularly, the non-toxic salt is calcium or magnesium stearate. Examples of other non-toxic salts which may be used are sodium, potassium or zinc salts of long-chain fatty acids such as stearic and palmitic acid. The amount of salt of medium or long-chain fatty acid in the mixture with the microorganism is suitably from about 5 to about 90 weight-%, preferably about 5 to about 80 wt.-%, more preferably about 5 to about 50 wt.-%, and most preferably about 5 to about 30 wt.-%, based on the dry weight of the microorganism. The ratio of edible oil, if present, to salt of a medium or long-chain fatty acid is suitably about 1:10 or lower, e.g., about 1:20 parts by weight.

The term compacting or compaction as used herein denotes any method to prepare a homogeneous, cohesive mixture of the components. The compaction is suitably carried out by kneading the microorganism together with the medium or long-chain fatty acid salt and, optionally, an edible oil, preferably a medium-chain (e.g., $C_{8-14}$) triglyceride, a tocopherol such as a-tocopherol, soy oil, palm oil, sunflower oil, or any other known edible oil, or mixtures thereof to provide an homogeneous paste. For granulation, the paste is formed into particles of appropriate size, e.g. about 10 μm to about 800 μm which are then submitted to coating. Alternatively, an intimate powderous mixture of the microorganism and the medium or long-chain fatty acid salt may be formed, e.g., by shaking. The powderous mixture wherein the microorganism particles are assumed to be overspread with the medium or long-chain fatty acid salt, e.g., magnesium stearate, is submitted to coating.

In the second step of the process of the invention, the granulate particles or the powder are coated. Coating may be accomplished by any coating technology with spraying a solution of the coating material into a fluidized bed of the powder or granules to be coated being a preferred method.

The coating material is suitably one, which can be dissolved or suspended in water as a viscous solution or suspension. Carbohydrates and proteins are suitable for this purpose. Examples of carbohydrates for use as coating material in the process of the present invention are polysaccharides such as alginate, pectin, starch, modified starch, maltodextrin, carrageenan, gum arabic, guar gum, xanthan, cellulose and cellulose derivatives, such as hydroxypropyl methylcellulose, hydroxypropyl methylcellulose phthalate and acetate-succinate, oligosaccharide, disaccharide and monosaccharide. Examples of proteins for use as coating material in the process of the present invention are gelatin, plant proteins and whey proteins The preferred coating material is sodium alginate which may by used as an about 0.1 to about 8 wt.-% aqueous solution. Other coating agents known in the art, especially those known to provide gastric juice resistant coatings may be used also, e.g. cellulose derivatives such as hydroxypropyl methylcellulose, hydroxypropyl methylcellulose phthalate and acetate-succinate.

The amount of coating is preferably 15 wt.-% or less based on the total weight of the composition, more preferably about 0.1 wt/-% to about 10 wt.-%, still more preferably about 0.1 wt. % to about 5 wt. %, and most preferably about 1 wt.-% to about 3 wt-%.

The microorganism used in the first step of the process of the present invention is suitably a freeze-dried preparation and may have a coating, especially a gastric juice resistant coating. Preferably, the microorganism used in the blending or compacting step has a coating or is embedded in matrix material. Alternatively other ways of drying the microorganism are possible such as spray drying, fluid bed drying. Such freeze-dried preparation of a microorganism, which has a gastric juice resistant coating may be obtained by treatment of a cell suspension of the microorganism with compounds at least selected from the group consisting of proteins (whey, milk, others), sugars (maltose, trehalose, lactose, sucrose), starch, cellulose, and optionally, other stabilizing or freeze protecting agents like ascorbic acid. More preferably, the cell suspension is treated with proteins, maltodextrins, trehalose, and optionally, other stabilizing or freeze protecting agents like ascorbic acid to form a viscous paste, which is submitted to freeze-drying. The so-obtained material is grinded to a size of about 10 μm to about 800 μm. In particular, the freeze-dried preparation may be obtained as described in Korean patents KR 429494B or KR 429495 B, the contents of which are incorporated herein by reference. Thus, in a particularly preferred embodiment, the invention is concerned with solid compositions containing a microorganism which is coated by or embedded within a salt of a medium or long-chain fatty acid, wherein the microorganism has a first coating layer below the coating by the salt of the medium or long-chain fatty acid; and which composition has an outer coating which contains substantially no material which is present inside the composition.

According to a preferred embodiment, the residual water concentration present in the composition after coating is below 10%. More preferably, the residual water concentration is below 5%, even more preferably below 4%. The residual water concentration is preferably measured by loss on drying. Preferably, this method is performed on 4 g product, at 70° C. during 60 minutes. According to another preferred embodiment, the water activity of the composition after coating is ranged between 0.04 and 0.3. More preferably, the water activity is ranged between 0.04 and 0.2, even more preferably between 0.04 and 0.15 and most preferably between 0.04 and 0.1. The water activity is preferably established at a given temperature by measuring the equilibrium relative humidity (erh) in the headspace of a closed chamber in which the powder is placed. The preferred temperature is 25° C. The water activity is expressed as being the erh divided by 100.

Accordingly to obtain such compositions with such low residual water concentrations or water activity, the final step of coating the granulate particles or the powder is simultaneously a drying step performed in a fluidised bed. Alternatively, the drying step is performed as an additional step after the coating of the granulate particles or the powder. Surprisingly, we found that compositions with a relatively low residual water concentrations or water activity exhibit much better survival of microorganisms during storage.

The compositions of the present invention may find use as a nutraceutical, i.e. a pharmaceutical product that has nutritional value or a food that has its nutritional value enhanced by a pharmaceutical (in casu: the microorganism) or as a nutritional ingredient, or as a health ingredient, or as a supplement to food or beverage or as a stand-alone medicament. Accordingly, in another embodiment, the invention relates to a food or beverage comprising a composition in accordance with the present invention. Such food or beverage may contain any physiologically or acceptable excipient and/or diluent. Preferred food products are cultured milk, yoghurt, cheese, milk powder, coveratures (defined as mixtures of oil, sugar(s) and milk protein (whey)), infant formulas, fermented meat product or a beverage such as milk drink, sport drink, fruit juices, fruit drinks.

According to another embodiment, the composition of the invention is in the form of a tablet, capsule, powder or granulate, orally liquid administered liquid preparation, suppositories, dry preparations. More preferably, the composition is in the form of an enteric tablet, capsule, powder or granulate that will survive the stomach and arrive intact in the intestine. All these forms can be prepared by known means, using food grade, respectively pharmaceutically acceptable carriers, excipients, solvents or adjuvants. For the preparation of the medicament, standard ingredients and method of preparation as already described in Remington: The science and practice of pharmacy, 1995, Mack Publishing, Co Easton, Pa. 18042, USA) can be used. Remington is herewith incorporated by reference.

Accordingly, according to a preferred embodiment, the process of the invention leads to the manufacture of a solid composition comprising a microorganism, wherein this composition has improved flowability and/or reduced hygroscopicity, compared to known solid compositions comprising a microorganism.

The invention is illustrated further by the Examples given below. Throughout the description and claims, the term "Lafti® L10" refers to a freeze-dried cell preparation of *Lactobacillus acidophilus* as defined earlier in the description. The medium chain triglyceride (MCT) consisted of a mixture of triglycerides of which no less than 95% are octanoic and decanoic acid (see Handbook of Pharmaceutical Excipients, $2^{nd}$ ed., Am. Pharm. Association, Wash., USA, 1994)

EXAMPLE 1

Compaction/Fluidized Bed Coating

Step 1:

Magnesium stearate (46.74 g), alpha-tocopherol (6.46 g) and medium chain triglyceride (MCT, 3.8 g) were mixed in a beaker and then kneaded with a pasta maker (Model Atlas 150, Fabrique En Italie Par, Campodarsego, Itali) till the mixture was homogeneous. The mixture was then mixed with Lafti® L10 (CBS 116411) (323 g) and kneaded with the pasta maker till it became homogenous and flaky. The flaky material was pressed through a 800-micron sieve to form granulated particles.

Step 2:

A 6% alginate solution was prepared by dissolving 7.372 g of sodium alginate (13% moisture content; FMC Biopolymer, Philadelphia, USA) in deionized water (99.5 g). The magnesium stearate-coated Lafti® L 10 (as obtained in Step 1, 350 g) was placed in a fluidized-bed granulator (MP-1 Multi-Processor, Aeromatic-Fielder, Bubendorf, Switzerland) and sprayed from bottom with the 6% alginate solution (106.9 g) at a rate of ca. 1.6 g per minute. At the end, the product was dried to a moisture content below 4% to give a final product with following particle size distribution as presented in table 1.

TABLE 1 particle size distribution

| Particle Size, micron | | | | | | | |
|---|---|---|---|---|---|---|---|
| >850 | >800 | >600 | >425 | >355 | >250 | >150 | <150 |
| % 13.1 | 2.5 | 15.9 | 15.3 | 7.4 | 15.2 | 21.9 | 8.7 |

The final product had the following composition as presented in table 2.

TABLE 2 composition of the final product

| | % |
|---|---|
| Lafti ® L10 | 83.47 |
| Mg stearate | 12.08 |
| Tocopherol | 1.67 |
| MCT | 0.98 |
| Na alginate | 1.8 |

Flowability: The flowability was determined by recording the time required for 100 g of the sample passing through a funnel with a neck of 11 cm in diameter. The flowability was 16 seconds per 100 g, whereas the unchanged Lafti® preparation had no powder flowability.

*Lactobacillus acidophilus* process survival rate is shown below in table 3. The number of cfu was estimated by enumeration of *Lactobacillus* colony formed on Mann Ragosa Sharp (MRS) (Oxoid, UK) agar, after incubation of inoculated agar plates at 37° C. for at least 48 hours under anaerobic conditions.

TABLE 3 survival rate of the probiotic in the composition

| | cfu/g |
|---|---|
| Lafti ® L10(unchanged preparation) | $220 \times 10^9$ |
| Expected Alginate/Magnesium stearate coated Lafti ® (Expected) | $184 \times 10^9$ |
| Alginate/Magnesium stearate coated Lafti ® L10(Determined) | $190 \times 10^9$ |
| Survival rate | 100% | cfu: colony forming units

EXAMPLE 2

Tabletting 2.80 g Polyplasdone XL10, (Crospovidone) and 181.96 g Avicel pH 302 (microcryst. cellulose) were sieved through a 1 mm sieve. 95.24 g of the Lafti® L10 preparation obtained according to Example 1 were added and mixed for 10 minutes with a tumbler mixer.

The tablet mixture was compressed to tablets on a single punch press (Comprex II) to oblong tablets (22 mm×9 mm) weighing about 1400 mg with a compression force of 20 kN. The characteristics of the tablets obtained were as follows:

| Crushing force: | 277 N (determined with Kraemer UTS 4.1) |
|---|---|
| Disintegration time: | 7 min. 10 sec. (according USP 27, demineralized water) |
| Added counts/tabl. | $90.8 * 10^9$ |
| Found counts /tabl. | $89.6 * 10^9$ (retention = 99%) |

The term "Added counts" refers to the number of microorganism counts (colony forming units) which were added with the Lafti® L10 preparation of Example 1; the term "Found counts denotes the colony forming units found in the tablet formulation.

EXAMPLE 3

Blending/Fluidized Bed Coating

Step 1:

Lafti® L 10 (272 g) and magnesium stearate (48 g) were placed in a 1-liter bottle and shaken for 20 minutes at 45 RPM (Turbula T2C, Willy A. Bachofen, Basel, Switzerland).

Step 2:

A 6% alginate solution was prepared by dissolving 6.321 g of sodium alginate (13% moisture content; FMC Biopolymer, Philadelphia, USA) in deionized water (85.3 g). The product obtained in Step 1 (300 g) was placed in a fluidized-bed granulator (MP-1 Multi-Processor, Aeromatic-Fielder, Bubendorf, Switzerland) and sprayed from the bottom with the 6% alginate solution (91.65 g) at a rate of 0.86-1.6 g per minute. At the end, the alginate and magnesium stearate-coated Lafti® L10 was dried to a moisture content below 4% to give a final product with following particle size distribution as presented in table 4.

TABLE 4

| particle size distribution | | | | | | | | |
|---|---|---|---|---|---|---|---|---|
| | Particle Size, micron | | | | | | | |
| | >850 | >800 | >600 | >425 | >355 | >250 | >150 | <150 |
| % | 0.2 | 0.1 | 0.9 | 11.5 | 11.6 | 23.5 | 28.5 | 23.7 |

The final product has the following composition as presented in table 5.

TABLE 5

| composition of the final product obtained | |
|---|---|
| | % |
| Lafti ® L 10 | 83.47 |
| Mg stearate | 14.73 |
| Na alginate | 1.8 |

Flowability: The flowability was determined as described in Example 1 and was 10 seconds per 100 g whereas the unchanged Lafti® preparation had no powder flowability.

*Lactobacillus acidophilus* process survival rate is shown below in table 6.

TABLE 6

| survival rate of the probiotic in the composition | |
|---|---|
| | cfu/g |
| Lafti ® L 10 | $140 \times 10^9$ |
| Expected Alginate/Magnesium stearate coated Latti ® L10 (Expected) | $117 \times 10^9$ |
| Alginate/Magnesium stearate coated Lafti ® L10(Determined) | $94 \times 10^9$ |
| Survival rate | 80% |

EXAMPLE 4

Tabletting 0.98 g Polyplasdone XL10, (Crospovidone), 55.09 g Avicel PH 302 (microcryst. cellulose) and 41.93 g Lafti® L 10 preparation obtained according to example 3 are sieved through a 1 mm sieve and mixed for 10 minutes with a tumbler mixer.

The tablet mixture was compressed to tablets on a single punch press (Comprex II) to oblong tablets (22 mm×9 mm) weighing about 1400 mg with a compression force of 20 kN.

The characteristics of the tablets obtained were as follows:

| | |
|---|---|
| Crushing force: | 254.4 N (determined with Kraemer UTS 4.1) |
| Disintegration time: | 52 min. 02 sec. (according USP 27, demineralized water) |

EXAMPLE 5

Step 1:

Lafti® L10 (272 g) and magnesium stearate (48 g) were placed in a 1-liter bottle and shaken for 20 minutes at 45 RPM (Turbula T2C, Willy A. Bachofen, Basel, Switzerland).

Step 2:

A 3% pectin solution was prepared by dissolving 16.45 g of pectin (GENU® pectin USP/100, 8.83% moisture content, CP Kelco, Lille Skensved, Denmark) in deionized water (483.55 g). The product obtained in Step 1 (360 g) was placed in a fluidized-bed granulator (MP-1 Multi-Processor, Aeromatic-Fielder, Bubendorf, Switzerland) and sprayed from the top with the 3% pectin (216 g) at a rate of about 1.5 g per minute. At the end, the pectin and magnesium stearate-coated Lafti® L10 was dried to a moisture content below 4%. The major fraction (301 g) of the product was in the granulator container, but a smaller fraction of whitish material (59 g) was retained in the filter. Based on the color (magnesium stearate: white, Lafti: brownish), the material in the filter was predominately magnesium stearate.

The particle size distribution of the combined fractions is presented in table 7.

TABLE 7

| particle size distribution | | | | | | | | |
|---|---|---|---|---|---|---|---|---|
| | Particle Size, micron | | | | | | | |
| | >850 | >800 | >600 | >425 | >355 | >250 | >150 | <150 |
| % | 0.1 | 0 | 0.35 | 0.61 | 2.08 | 20.38 | 36.16 | 40.33 |

Flowability: The flowability was determined by recording the time required for 100 g of the sample passing through a funnel with a neck of 11 cm in diameter. The flowability was 21 seconds per 100 g, whereas the unchanged Lafti® L10 preparation had no powder flowability.

The product has the following composition as presented in table 8.

TABLE 8

| composition of the final product obtained | |
|---|---|
| | % |
| Lafti ® L10 | 83.47 |
| Mg stearate | 14.73 |
| Na alginate | 1.8 |

When the minor fraction retained in the filter is removed, the particle size distribution of the product is as shown in table 9.

TABLE 9

| particle size distribution | | | | | | | |
|---|---|---|---|---|---|---|---|
| Particle Size, micron | | | | | | | |
| >850 | >800 | >600 | >425 | >355 | >250 | >150 | <150 |
| 0.11 | 0 | 0.42 | 0.73 | 2.49 | 24.38 | 43.25 | 28.63 |

(% row)

Flowability: The flowability was determined by recording the time required for 100 g of the sample passing through a funnel with a neck of 11 cm in diameter. The flowability was 14 seconds per 100 g, whereas the unchanged Lafti® preparation had no powder flowability.

EXAMPLE 6

Compaction/Fluidized Bed Coating

Step 1:
Calcium stearate (61.5 g), alpha-tocopherol (8.5 g) and medium chain triglyceride (MCT, 5 g) were mixed in a beaker and then kneaded with a pasta maker (Model Atlas 150, Fabrique En Italie Par, Campodarsego, Itali) till the mixture was homogeneous. The mixture was then mixed with Lafti® L10 (425 g) and kneaded with the pasta maker till it became homogenous and flaky. The mixture was compacted with a tablet press and the tablets were crushed and passed through a 1-mm screen. The process was repeated totally 4 times. In the last time, the mixture was pressed through a 500-micron sieve to form granulated particles.

Step 2:
An alginate solution was prepared by dissolving 33 g of sodium alginate (13% moisture content; FMC Biopolymer, Philadelphia, USA) in deionized water (538.9 g). The magnesium stearate-coated Lafti®L 10 (as obtained in Step 1, 350 g) was placed in a fluidized-bed granulator (MP-1 Multi-Processor, Aeromatic-Fielder, Bubendorf, Switzerland) and sprayed from bottom with the alginate solution (142.9 g) at a rate of ca. 2.3 g per minute. At the end, the product was dried to a moisture content below 4%. The fraction above 850 microns was removed, which represented 8.1% of the total material. The particle size distribution of the rest of material is shown in table 10.

TABLE 10

| particle size distribution | | | | | | | |
|---|---|---|---|---|---|---|---|
| Particle Size, micron | | | | | | | |
| >850 | >800 | >600 | >425 | >355 | >250 | >150 | <150 |
| 0.1 | 1.1 | 26.3 | 32.5 | 13.2 | 16.8 | 7.2 | 2.9 |

The final product had the following composition as presented in table 11.

TABLE 11

| composition of the final product obtained | |
|---|---|
| | % |
| Lafti ® L10 | 83.3 |
| Mg stearate | 12.05 |
| Tocopherol | 1.67 |
| MCT | 0.98 |
| Na alginate | 2.0 |

Flowability: The flowability was determined by recording the time required for 100 g of the sample passing through a funnel with a neck of 11 cm in diameter. The flowability was 14 seconds per 100 g, whereas the unchanged Lafti® preparation had no powder flowability.

EXAMPLE 7

Blending/Fluidized Bed Coating

Step 1:
Lafti® L 10 (272 g) and magnesium stearate (48 g) were placed in a 1-liter bottle and shaken for 20 minutes at 45 RPM (Turbula T2C, Willy A. Bachofen, Basel, Switzerland).

Step 2:
A 3% alginate solution was prepared by dissolving 6.321 g of sodium alginate (13% moisture content; FMC Biopolymer, Philadelphia, USA) in deionized water (176.9 g). A 5% calcium chloride was prepared by dissolved 5 g of calcium chloride in deionized water (95 g). The product obtained in Step 1 (300 g) was placed in a fluidized-bed granulator (MP-1 Multi-Processor, Aeromatic-Fielder, Bubendorf, Switzerland) and sprayed from the top with the 3% alginate solution (180 g) at a rate of 1-3 g per minute and with the 5% calcium chloride solution (27 g) at a rate of 0.5-2 g per minute. At the end, the alginate and magnesium stearate-coated Lafti® L10 was dried to a moisture content below 4% to give a final product with following particle size distribution as presented in table 12.

TABLE 12

| particle size distribution | | | | | | | |
|---|---|---|---|---|---|---|---|
| Particle Size, micron | | | | | | | |
| >850 | >800 | >600 | >425 | >355 | >250 | >150 | <150 |
| 0 | 0 | 0.4 | 11.9 | 15.6 | 30.5 | 29.5 | 11.9 |

The final product has the following approximate composition as shown in table 13.

TABLE 13

| composition of the obtained product | |
|---|---|
| | % |
| Lafti ® L 10 | 83.4 |
| Mg stearate | 14.7 |
| Na/Ca alginate | 1.84 |

Flowability: The flowability was determined as described in Example 1 and was 16 seconds per 100 g whereas the unchanged Lafti®preparation had no powder flowability.

EXAMPLE 8

Tabletting 0.98 g Polyplasdone XL10, (Crospovidone), 55.09 g Avicel PH 302 (microcryst. cellulose) and 41.93 g Lafti® L 10 preparation obtained according to example 6 are sieved through a 1 mm sieve and mixed for 10 minutes with a tumbler mixer.

The tablet mixture was compressed to tablets on a single punch press (Comprex II) to oblong tablets (22 mm×9 mm) weighing about 1400 mg with a compression force of 20 kN.

The characteristics of the tablets obtained were as follows:
Crushing force: 254.4 N (determined with Kraemer UTS 4.1)

EXAMPLE 9

The aim of those trials was to validate the Lafti formulation and process on a pilot scale and its possible extrapolation to the production scale.

Premix Recipe

Three trials were done in order to test the sensibility of the premix to the oil quantity as presented in table 14.

TABLE 14 composition of the three premixes prepared

|  | A | D | F |
|---|---|---|---|
| Size of the batch | 10.1 Kg | 9.9 Kg | 10.2 Kg |
| dl-alpha tocopherol | 13.1% | 12.1% | 13.7% |
| MCT | 7.7% | 7.1% | 8.1% |
| Calcium stearate | 79.2% | 80.8% | 78.2% |
| Deposit on the wall | no | no | no |
| Deposit on the impeller | no | no | no |

The oil mix was sprayed on the calcium stearate, which was mixed in a high shear mixer at 150 rpm. The high shear mixer could be emptied in each case without problem (no deposits). The premix contained no lumps and no sieving was necessary.

Powder Mixture

The powder mixture (lafti L10/premix) was also realised in the high shear mixer with the following recipe presented in table 15.

TABLE 15 powder mixtures realized starting from the three premixes

| | Trial | | | |
|---|---|---|---|---|
| | B | C | E | G |
| Premix lot | A | A | D | F |
| Premix kg | 1.237 | 1.237 | 1.236 | 1.238 |
| Lafti L10 kg | 7 | 7 | 7 | 7 |

The powder mixture was then compacted on a Bepex compactor.

Pressure used: 5-20 kN, number of passes: 2

The compressed material was then sieved as presented in table 16. The rotary sieve used for the last 2 trials enabled the sieving of the 8-9 Kg in less than 5 minutes.

TABLE 16

Sieving conditions of the five trials

| | Trial | | | |
|---|---|---|---|---|
| | B | C | E | G |
| Sieve | Vibrating, 500 | Vibrating, 500 | Rotating, 1000 | Rotating, 500 |

The compacted/sieved material was coated in a fluid bed coater (Aeromatic). The bottom spray configuration was used. A 4% alginate solution was found the optimum to be easily sprayed. Table 17 gives an overview of the characteristics of the process used in each trial.

TABLE 17 process used for each trial

| | Trial | | | |
|---|---|---|---|---|
| | B | C | E | G |
| bed | Compacted B | Compacted C | Compacted E | Compacted G |
| quantity | 7 Kg | 7 Kg | 7 Kg | 7 Kg |
| Alginate sprayed | 3070 g | 3240 g | 3100 g | 3240 g |
| Spraying T° | 21-28° C. | 20-26° C. | 21-27° C. | 20-26° C. |
| Drying T° | Up to 37.5° C. | Up to 38.2° C. | Up to 38.0° C. | Up to 39.5° C. |
| Spraying time | 155 min. | 169 min. | 151 min. | 159 min. |
| Drying time | 50 min. | 91 min. | 69 min. | 81 min. |
| Yield | 80.7% | 92.6% | 96.3% | 89.4% |

Final Product Quality

All the products obtained have good to very good flowing properties and are easy to use to make good properties tablets. The density of the product is high which is good for the packaging.

The granules obtained are not hygroscopic and can be left in the open air several days without sticking together. The particle size distribution is good especially for trial C.

The measurement of the survival rate after the granulation process and after the tabletting process is good and is comparable with the data obtained in table 3 or 6.

Table 18 gives an overview of the characteristic of the products produced in the five trials.

TABLE 18 characteristics of products prepared in the five trials

| | B | C | E | G |
|---|---|---|---|---|
| Water activity (60 min) | 0.133 | 0.045 | 0.127 | 0.051 |
| Moisture content (%) | | | | |
| (4 g/70° C./30 min) | 3.65 | 3.08 | 3.42 | 3.07 |
| (4 g/70° C./60 min) | 4.12 | 3.51 | 3.89 | 3.49 |
| Particle size (%) | | | | |
| >850 | 5.3 | 3.8 | 23.5 | 2.2 |
| 800-850 | 1.1 | 0.8 | 4 | 0.6 |
| 600-800 | 12.6 | 10.2 | 17.9 | 7.2 |
| 425-600 | 33.8 | 24 | 20.6 | 22.9 |
| 355-425 | 11.6 | 18.1 | 11.7 | 18.6 |
| 250-355 | 16.5 | 25.6 | 11.2 | 30.4 |
| 150-250 | 9.3 | 7.7 | 2 | 9.1 |
| <150 | 1.1 | 1.1 | 0.3 | 0.3 |
| Tablets (20 KN) | 168.3 | 165.4 | 163.3 | 176 |
| Bulk density (ml/g) | 0.5 | 0.53 | 0.53 | 0.48 |
| Tapped density | 0.61 | 0.63 | 0.65 | 0.56 |
| Flowability 14 mm | 1000 | 1000 | 1200 | 1000 |
| Flowability 11 mm | 462 | 429 | 545 | 500 |
| Flowability 9 mm | 240 | 240 | 273 | 250 |
| Flowability 7 mm | 125 | 128 | 150 | 136 |

The invention claimed is:
1. A process for the manufacture of a solid composition comprising coated microorganism-containing particles, which process comprises:
(a) blending and/or compacting in a first step a microorganism with a salt of a medium or long-chain fatty acid to form a powderous mixture or compacted granulate comprised of microorganism-containing particles;
(b) at least partially coating the microorganism-containing particles in a second step with a water-soluble coating to obtain coated microorganism-containing particles having a particle size of between 10 μm to about 800 μm; and (c) forming a solid composition comprised of the coated microorganism-containing particles.

2. A process as in claim 1 wherein the first step comprises compacting and granulating the microorganism and the salt of a medium or long-chain fatty acid to form a compacted granulate comprised of the microorganism-containing particles.

3. A process as in claim 1 wherein the salt of the medium or long-chain fatty acid is magnesium stearate.

4. A process as in claim 1 wherein the salt of the medium or long-chain fatty acid is calcium stearate.

5. A process as in claim 2, wherein compacting of the microorganism and the salt of a medium or long-chain fatty acid is carried out in the presence of an edible oil.

6. A process as in claim 5 wherein the edible oil is selected from medium chain triglycerides and tocopherols, and mixtures thereof.

7. A process as in claim 1, wherein the first step comprises blending the microorganism with the salt of a medium or long-chain fatty acid to produce a powderous mixture.

8. A process as in claim 1, wherein the water-soluble coating comprises an alginate.

9. A process as claim 8, wherein the coating is applied by spraying an aqueous alginate solution on the microorganism-containing particles.

10. A process as in claim 1 wherein the microorganism is a probiotic or a mixture thereof.

11. A process as in claim 1 wherein the microorganism is a freeze-dried preparation.

12. A process as in claim 1, wherein the microorganism has a coating of or is embedded in a matrix material.

13. A process as in claim 12 wherein the matrix material is selected from proteins, maltodextrins, trehalose and/or ascorbic acid.

14. A process as in claim 1 wherein the microorganism is a *Bifidobacterium, Lactobacillus, Propionibacterium*, or *Enterococcus*.

15. A process as in claim 1 wherein the microorganism is selected from the group consisting of *Bifidobacterium infantis, Bifidobacterium longum, Bifidobacterium animalis, Bifidobacterium lactis, Lactobacillus acidophilus, Lactobacillus rhamnosus, Lactobacillus casei, Lactobacillus paracasei* and *Lactobacillus helveticus*.

16. A process as in claim 15 wherein the microorganism is selected from the group consisting of *Lactobacillus acidophilus* CBS 116411, *Bifidobacterium animalis* and *Lactobacillus casei* CBS 116412.

17. A solid composition comprising coated microorganism-containing particles, wherein the coated microorganism-containing particles comprise a microorganism and a coating on the microorganism which is comprised of a salt of a medium or long-chain fatty acid, wherein the coated microorganism-containing particles have, optionally, a first coating layer below the coating by the salt of the medium or long-chain fatty acid, and wherein the microorganism-containing particles have an outer coating which contains substantially no material which is present inside the particles, and wherein the coated microorganism particles have a particle size of between about 10 μm to about 800 μm.

18. A composition as in claim 17, wherein the microorganism is a freeze-dried preparation.

19. A composition as in claim 17, wherein the microorganism has a first coating layer below the coating by the salt of the medium or long-chain fatty acid.

20. A composition as in claim 19 wherein the first coating layer has been provided by treatment of a cell suspension of the microorganism with proteins, maltodextrins, trehalose and ascorbic acid.

21. A composition as in claim 17, which is in the form of a granulate or powder.

22. A composition as in claim 17, which is in the form of a tablet.

23. A composition as in claim 17, wherein the salt of the medium or long-chain fatty acid is magnesium or calcium stearate and the outer coating is sodium alginate.

24. A composition as in claim 17, wherein the microorganism is a probiotic or mixture thereof.

25. A composition as in claim 22 wherein the microorganism is a *Bifidobacterium, Lactobacillus, Propionibacterium*, or *Enterococcus*.

26. A composition as in claim 25 wherein the microorganism is selected from the group consisting of *Bifidobacterium infantis, Bifidobacterium longum, Bifidobacterium animalis, Bifidobacterium lactis, Lactobacillus acidophilus, Lactobacillus rhamnosus, Lactobacillus casei, Lactobacillus paracasei* and *Lactobacillus helveticus*.

27. A composition as in claim 26 wherein the microorganism is selected from the group consisting of *Lactobacillus acidophilus* CBS 116411, *Lactobacillus casei* CBS 116412 and *Bifidobacterium animalis*.

28. A composition as in claim 17, wherein the water activity is ranged between 0.04 and 0.3.

29. A food comprising a composition as in claim 17.

30. A food according to claim 29 which is cultured milk, yoghurt, cheese, milk powder, coveratures, infant formulas, fermented meat product or a beverage.

31. A food according to claim 30, wherein the coverature is a mixture of oil, sugar, and milk protein.

32. A food according to claim 31, wherein the milk protein is whey.

33. A food according to claim 30, wherein the beverage is selected from the group consisting of milk drinks, sport drinks, fruit juices and fruit drinks.

34. A medicament, nutraceutical, nutritional health ingredient or a health ingredient comprising a composition as in claim 17.

* * * * *